(12) United States Patent
Vaillancourt

(10) Patent No.: US 6,699,221 B2
(45) Date of Patent: Mar. 2, 2004

(54) BLOODLESS CATHETER

(76) Inventor: Vincent L. Vaillancourt, 14 Bunyan Dr., Livingston, NJ (US) 07039

( * ) Notice: Subject to any disclaimer, the term of this patent is extended or adjusted under 35 U.S.C. 154(b) by 0 days.

(21) Appl. No.: 09/879,872

(22) Filed: Jun. 12, 2001

(65) Prior Publication Data

US 2001/0053895 A1 Dec. 20, 2001

Related U.S. Application Data

(60) Provisional application No. 60/211,733, filed on Jun. 15, 2000.

(51) Int. Cl.[7] .............................................. A61M 5/178
(52) U.S. Cl. ........................... 604/167.01; 604/167.03; 604/167.04; 604/167.06; 604/164.13
(58) Field of Search ....................... 604/167.01, 167.04, 604/167.02, 167.03, 167.06, 171, 164.01, 164.07, 164.13

(56) References Cited

U.S. PATENT DOCUMENTS

| 4,387,879 | A | * | 6/1983 | Tauschinski | 251/149.1 |
|---|---|---|---|---|---|
| 4,874,377 | A | * | 10/1989 | Newgard et al. | 251/149.1 |
| 5,064,416 | A | * | 11/1991 | Newgard et al. | 604/167.03 |
| 5,269,764 | A | * | 12/1993 | Vetter et al. | 251/149.1 |
| 5,360,417 | A | * | 11/1994 | Gravener et al. | 604/278 |
| 5,657,963 | A | * | 8/1997 | Hinchliffe et al. | 251/149.1 |
| 5,895,377 | A | * | 4/1999 | Smith et al. | 604/256 |
| 5,957,898 | A | * | 9/1999 | Jepson et al. | 128/912 |
| 6,024,729 | A | * | 2/2000 | Dehdashtian et al. | 604/167.04 |
| 6,193,670 | B1 | * | 2/2001 | Van Tassel et al. | 600/486 |
| 6,261,282 | B1 | * | 7/2001 | Jepson et al. | 128/912 |

* cited by examiner

Primary Examiner—Brian L. Casler
Assistant Examiner—Jeremy Thissett
(74) Attorney, Agent, or Firm—Francis C. Hand; Carella, Byrne, Bain et al.

(57) ABSTRACT

The over-the-needle catheter is provided with a septum seal within the hub of the catheter. The introducer needle passes through the septum seal and into the catheter. Upon removal of the introducer needle, the septum seal reseals so that blood is prevented from flowing from the patient out of the hub. A male luer adaptor is used to form a connection, for example, to an IV bag by pushing the seal onto a tube secured within the hub and communicating with the catheter or, in another embodiment, by pushing a piercing ring through a slit in the septum seal to form a permanent lumen.

20 Claims, 5 Drawing Sheets

BLOODLESS CATHETER

This application claims the benefit of U.S. Provisional Application 60/211,733, filed Jun. 15, 2000.

This invention relates to a bloodless catheter. More particularly, this invention relates to a bloodless over-the-needle catheter.

Various types of over-the-needle catheters have been known for use as venipuncture devices and, particularly, for intravenous infusion purposes. Typically, these devices have been fabricated of a needle that is connected to a hub and a catheter that passes over the needle and is fixed as by a friction fit at an exposed end of the needle. The catheter is also fixed to a hub that receives the needle hub. Additional structure is also provided to form a closed chamber about the ends of the two hubs.

After implanting of the needle and catheter in a patient, the needle is usually removed while the catheter remains in place. A connection is then made between an I.V. line and the catheter in order to allow for the infusion of liquids and/or medicaments into the patient.

In almost all hospitals, there is a policy that once a catheter is in place and a connection made, that connection is never broken. With that as a design criteria, then there is no need for a bloodless catheter to have a reseal capability beyond the initial closure following the removal of the needle. In other words, there is a need only for the hub to somehow seal itself off from the outside environment when the needle is removed and then re-opened to allow fluid flow when a connection is made, e.g. by means of a male luer connector. The male luer connector is attached only once and never removed from the catheter hub. If per chance the male luer connector has to be removed in an emergency situation, then it would be permissible for blood to back flow through the catheter.

U.S. Pat. Nos. 5,330,435 and 5,234,410 describe different types of over-the-needle catheters which employ an elastomeric valve on a tube of the catheter to seal off the cannula of the catheter.

U.S. Pat. No. 5,211,634 describes a composite seal structure which is used in a coupling between a syringe and a line to a vein in a patient.

U.S. Pat. No. 5,487,728 describes the use of a seal having a resilient collapsible tubular portion and a septum at one end for sealing off a needle in a female luer connector.

Accordingly, it is an object of the invention to provide product which would meet these needs and be substantially less complicated, less costly to make and assemble than the previously known products.

Briefly, the invention is directed to a bloodless catheter comprised in part of a hub having a bore at a proximal end and a cannula fixed in and extending from an opposite distal end of the hub.

In accordance with the invention, a septum seal with a weakened central section is mounted in the bore of the hub in circumferentially sealed relation to prevent a flow of fluid from the cannula to the proximal end of the hub.

A means is also provided in the hub for forming a flow path through the weakened section of the seal in response to a relative movement between this means and this seal.

In use, a second means is provided for moving the first means relative to the seal in order to define a flow path through the seal.

In one embodiment, the means in the hub for forming a flow path is in the form of a tube which is mounted in the weakened section of the seal and which extends into the cannula. In addition, the means for moving the tube relative to the seal constitutes a male luer adaptor which can be slidably mounted in the bore of the hub in sealed relation and disposed concentrically about the tube. In this case, the forward end or nose of the adaptor engages and pushes the septum seal along the tube while the seal dilates about the slit in the weakened section of the seal.

In this embodiment, after the introducer needle and associated hub have been removed, the seal prevents any flow of blood from a patient through the hub.

In another embodiment, the means for forming a flow path through the weakened section of the seal is in the form of a piercing ring that is mounted on the seal for pushing through the weakened section of the seal in a direction towards the cannula in order to define a flow path through the seal. In this embodiment, a male luer adaptor may also be used as the means to move the piercing ring relative to the seal. In this case, the male luer adaptor is sized to engage and push the piercing ring through a slit in the septum seal in order to communicate the adaptor with the cannula.

Typically, in order to form an over-the-needle catheter, a needle hub is telescopically mounted in the bore of the hub while an introducer needle is fixed in the needle hub and extends through the cannula. In use, the introducer needle and catheter are introduced into a patient in the usual manner. Thereafter, the introducer needle and associated hub are withdrawn. At this time, the seal closes on itself to seal off the cannula from the proximal end of the first hub so that blood cannot flow from the patient out of the hub.

These and other objects and advantages of the invention will become more apparent from the following detailed description taken in conjunction with the accompanying drawings wherein.

Figure 1:
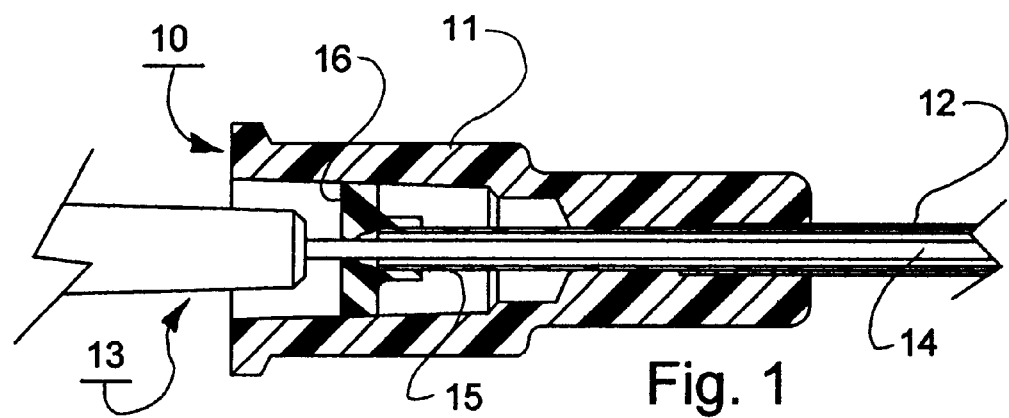
FIG. 1 illustrates a cross-sectional view of a product constructed in accordance with the invention for use as an over-the-needle catheter.

Referring to FIG. 1, the product 10 is constructed in the manner of an over-the-needle catheter with a hub 11, a cannula 12, e.g. a needle with a sharpened tip, made of metal or plastic, which is fixed in and which extends from the hub 11, a needle hub 13 and an introducer needle 14 which is fixed in the needle hub 13 and which extends coaxially through the cannula 12. The distal end of the needle 14 extends through the distal end of the cannula 12 and is secured thereto in a friction fit manner as is known. The construction of the hubs 11, 13, cannula 12 and needle 14 are conventional and need not be further described.

The product 10 also has a tube 15, for example of metal, which is secured internally within the catheter hub 11 and on which a septum seal or adaptor 16, for example of an elastomeric material is mounted. As indicated, the tube 15 is fixed within the catheter hub 11 and extends to a point within the plastic cannula 12. The tube 15 is otherwise of a size to permit passage of the needle 14.

Figure 2:
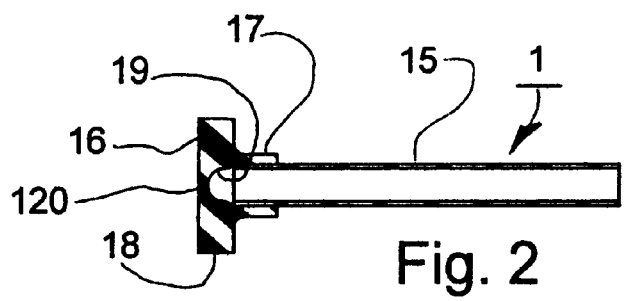
FIG. 2 illustrates a cross-sectional view of a seal and tube arrangement used in the product of FIG. 1 in accordance with the invention.
Figure 3:
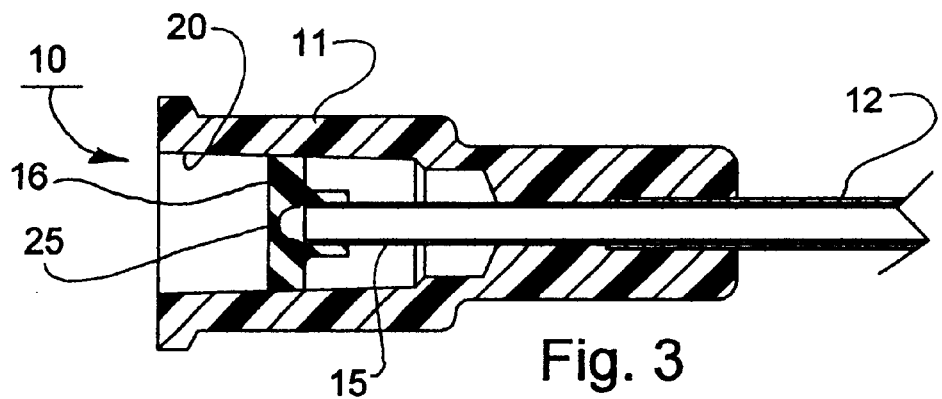
FIG. 3 illustrates a view similar to FIG. 1 with the introducer needle removed.

Referring to FIG. 2, the septum seal 16 is of generally T-shaped construction having a tubular portion 17 which fits over the tube 15 in a stretch-fit manner. In addition, the seal 16 has a cap 18 integral with the tubular portion 17. This cap 18 has an internal recess 19 which defines, in part, a weakened section 120 of the cap 18 within which a slit (not shown) may be formed to function as a valve. The seal 16 is placed over the tube 15 in an interference condition. Prior to this operation, the seal 16 is pierced to form a slit through which the needle 14 passes or alternately may be pierced directly by the needle 14. The purpose of the seal 16 to tube 15 seal (interference fit) is to prevent fluid from entering the space distal to the location of the seal 16.

The seal 16 is larger in diameter than the hub wall where the seal 16 is positioned is compressed thereby forming a pressure seal around the needle 14. In one example, the tube 15 has an outside diameter of 0.045", the tubular portion 17 of the seal 16 has an inner diameter of 0.037" and the cap 18 of the seal 16 has an outer diameter of 0.165" and a length of 0.040". In the sealed position, the hub wall where the seal 16 is positioned is of a diameter of 0.155". The compression on the seal 16 is thus 0.010" or approximately 6%. Under these conditions, the leakage pressure exceeds 10 psi.

Referring to FIG. 1, the seal 16 is located in a recessed manner within a tapered bore 20 of the hub 11 and is disposed in a circumferentially sealed relation, e.g. in an interference fit manner to the bore 20 of the hub 11 to prevent a flow of fluid from the cannula 12 to the proximal end of the hub 11.

As shown in FIG. 1, the needle 14 passes through the cap 18 of the seal 16 in a seal tight manner.

The interference fit between the seal 16 and the hub 11 is such that when the needle 14 is withdrawn, the seal 16 closes providing a leak proof seal to any blood which may pass back up through the catheter 12. The seal between the seal 16 and the tube 15 is sufficient to prevent fluid (blood) from exiting the tube 15 and passing into the space adjacent to the tube 15 within the catheter hub 11.

The interference fit between the cap 18 of the seal 16 and the bore 20 of the catheter hub 11 determines the maximum pressure allowable in the catheter 12 before leakage into the proximal end of the hub 11 occurs.

The tube 15 functions as a means in the hub for forming a flow path through the weakened section 120 of the septum seal 16 in response to a relative movement between the tube 15 and the seal 16.

A means is also provided for moving the tube 15 relative to the seal 16. For example, this means may be in the form of a male luer connector 21.

Figure 4:
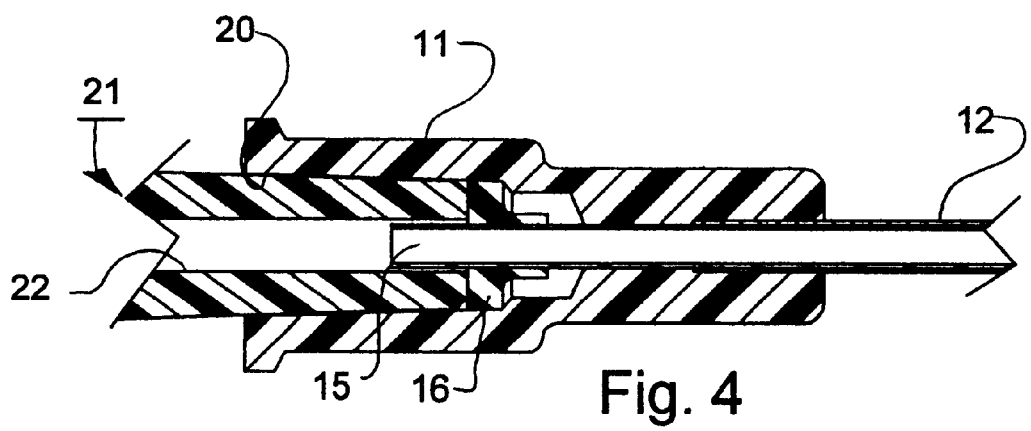
FIG. 4 illustrates a view similar to FIG. 3 of the product connected to a male luer connector in accordance with the invention.

Referring to FIG. 4, the product 10 may be connected to an I.V. line, for example, via a male luer connector 21 having an internal bore 22 of a size to slide over the tube 15. As indicated in FIG. 4, when the male luer connector 21 is slid into the catheter hub 11, the nose of the male luer connector 21 pushes the seal 16 into the interior of the hub 11 while sliding the seal 16 along the tube 15. During this time, the weakened section 120 of the cap 18 of the seal 16 expands radially so as to move about the open end of the tube 15.

After pushing the seal 16 over the tube 15 and down to the base of the catheter hub 11, the male luer connector 21 bottoms against the seal 16 as shown in FIG. 4. while dilating over the open end of the cannula 12. As shown in FIG. 4, a path for fluid flow is thus defined between the male luer connector 21 and the cannula 12. This path is not restrictive and is straight through with no significant decrease in cross section.

A seal is thus created between the septum seal 16 and the nose of the male luer connector 21 obviating the necessity for the male luer taper having to create an interference fit with the female luer taper of the hub 11 to effect a seal. In this manner, normal luer connector tolerances are not required with regard to the hub 11 (female luer connector) in order to obtain an effective seal to a conventional male luer connector.

This is a one time use seal. By this is meant that upon assembly with the seal 16 sitting on top of the tube 15 and the needle 14 penetrating the face wall of the seal 16, there is a seal between the needle 14 and seal 16. Upon removal of the needle 14, the opening created is closed due to the compressive action of the interference fit of the seal cap 18 and wall of the hub 11. When the male luer connector 21 is connected to the hub 11, the seal 16 is forced over the tube 15 permanently creating a through hole which is always larger than the tapered bevel portions of the (not shown) lumen of the cannula 12 to which the hub 11 is attached. Upon removal of the male luer connector 21, the seal 16 remains in place and the cannula 12 continues to be in fluid communication with the proximal portion of the hub 11.

Another advantage of the construction is the elimination of the need for the practitioner to apply digital pressure to the catheter 12 upon removal of the needle 14 from the catheter assembly. The elimination of this requirement in the catheterization procedure changes the procedure from one requiring extreme hand and finger dexterity to one that can easily be performed by a person who has normal skill. It has been long recognized that venipuncture using an over-the-needle catheter requires above average skill and much practice. As a result, many hospitals only allow certain nurses adept and trained in this art to perform these procedures. In some quarters, the procedure is referred to as a "three handed procedure" whereas only two hands are available.

Another advantage of the construction is the isolation of the blood from within the catheter hub 11. The blood may only travel up the tube 15 to the seal 16 where a seal is affected. Thus, there is never any blood within the hub 11 even after the seal is opened by the male luer connector 21. Any blood that may enter a portion of the tube 15 is immediately swept back into the blood vessel upon the initiation of flow upstream from the male luer connector 21.

When the male luer connector 21 is engaged with the hub 11 (female luer), the dead space is the annular volume between the top of the luer lumen and the outer diameter of the tube 15. This space is initially filled with fluid coming from the male luer connector 21 and, in most cases, does not exceed a micro drop of fluid. Thus, there is never any patient's blood in the hub 11 where the blood may stagnate, form a clot and eventually return to the blood vessel.

Figure 5:
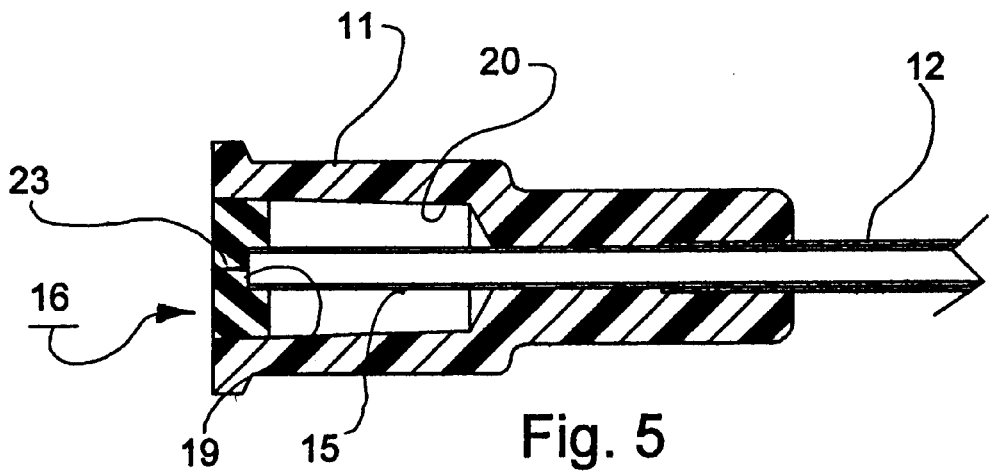
FIG. 5 illustrates a cross-sectional view of a modified product having a modified seal located at an open end of a catheter hub in accordance with the invention.

Referring to FIG. 5, wherein like reference characters indicate like parts as above, the seal 16' is constructed as a simple "septum" positioned at the entrance to the hub 11 (female luer adaptor). In this embodiment, the seal 16' is in the form of a disk having a tapered outer periphery, a weakened section defined by a coaxial recess 19' on one side to receive the tube 15' and a slit 23 centrally of the recess 19' to act as a valve. As shown, the tube 15' is elongated and has a tapered end to fit into the recess 19' of the seal 16' in a seal-tight manner.

Figure 6:
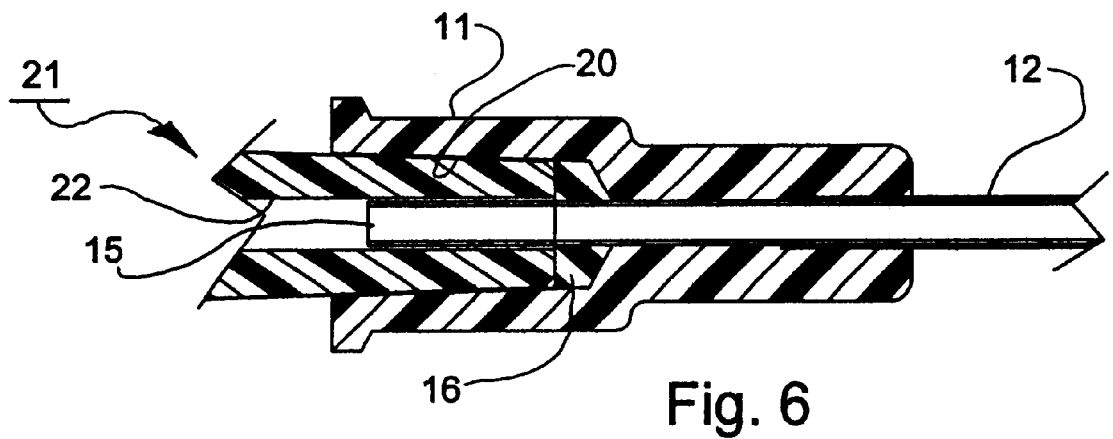
FIG. 6 illustrates a view similar to FIG. 5 of the modified product connected to a male luer connector in accordance with the invention.

Referring to FIG. 6, wherein like reference characters indicate like parts as above, when a connection is desired, the nose of a male luer connector 21 pushes the "septum" 16' along the outside of the tube 15' while the central portion of the seal 16' opens radially about the slit 23 allowing the connector 21 to slide over the tube 15'. A fluid flow path is thus effected from the connector 21 into the tube 15' and, thus, the cannula 12. This is a one time use since the seal 16' will not return to reseal once the seal 16' has been bottomed by the male luer connector 21.

The advantages of this construction include the ability to swab the face of the seal 16' thereby rendering the face sterile prior to connection and simplicity of manufacture. The product of this construction can be readily used as a female portion of the connector of the product of U.S. Pat. No. 5,122,123 to complete an inexpensive one time use sterile coupling.

Other uses include the use of the seal and tube in the hub of an introducer needle for catheter procedures, guide wires, and the like. In these cases, when the needle is removed, blood continues to be contained. A guide wire may be passed down through the seal slit (hole) which being an elastomeric structure will give sufficiently to allow passage of the guide wire and concurrently effect a seal with the guide wire to prevent blood flow. Upon removal of the introducer needle, the external skin of the patient behaves as a secondary seal until the procedure (Seldinger) is completed. In like manner, the sealed hub can be used for placement of spinal needles prior to infusion generally of pain control drugs or removal of CSF (cerebral spinal fluid).

The embodiment of FIGS. 1 to 4 corresponds to a product known as a bloodless catheter in which the blood does not exit the hub 11 when the introducer needle 14 is removed. The embodiment of FIGS. 5 and 6 corresponds to a product known as a swabable valve connector, the advantage of which is that it can be rendered sterile by swabbing prior to coupling (connection). This is ideally suited for one time use with a sterile connector as described in U.S. Pat. No. 5,122,123. Either basic construction may be used with the usual applications for spinal, central lines (Seldinger), and the like.

Figure 8:
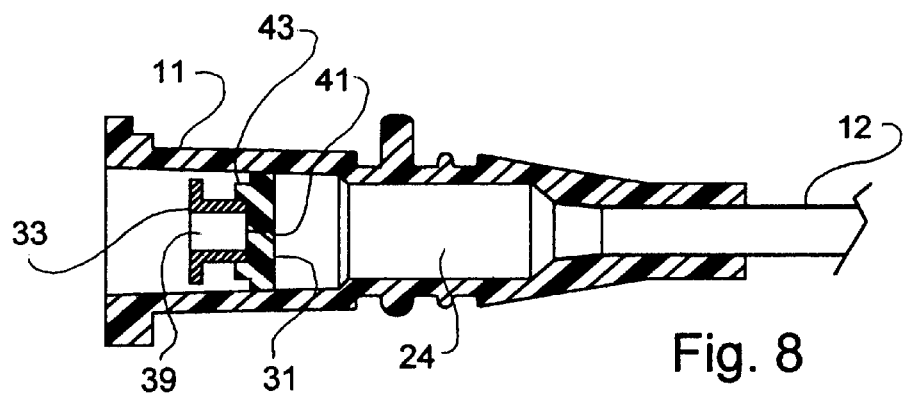
FIG. 8 illustrates a cross-sectional view of the embodiment of FIG. 7 with the catheter and associated hub removed.
Figure 7:
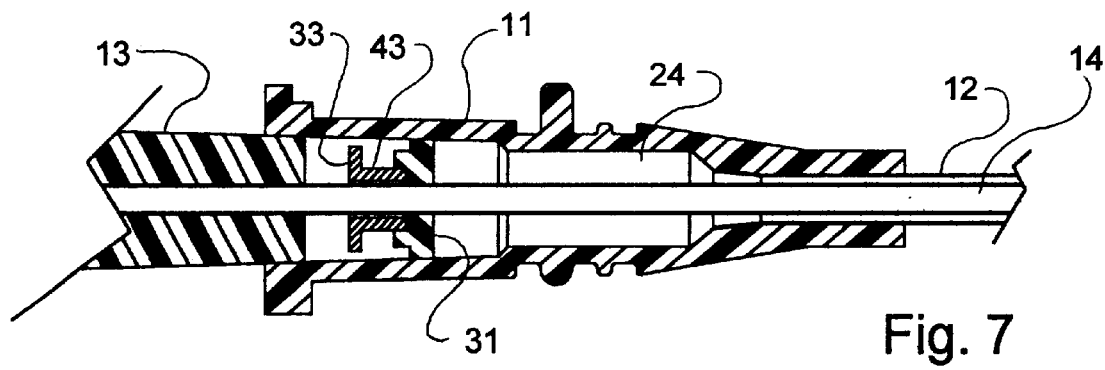
FIG. 7 illustrates a cross-sectional view of a second embodiment of an over-the-needle catheter employing a seal and piercing ring in accordance with the invention.

Referring to FIG. 8, wherein like reference characters indicate like parts as above, the bloodless catheter may be made such that a septum seal 31 is positioned in the bore 24 of a catheter hub 11 in circumferentially sealed relation just prior to inserting an introducer needle assembly 12, 13 (FIG. 7). As indicated, the seal 31 has a centrally located weakened section defined by a slit 41 that defines a valve and the outer diameter of the seal 31 is sized to be larger than the inner diameter of the bore 24 of the hub 11 such that a compressive force is exerted on the internal portion of the seal 31 so that the slit 41 is closed.

In addition, a means in the form of a piercing ring 32 is mounted in the hub 11 on the seal 31 on the side facing the distal end of the hub 11 for forming a flow path through the weakened section 41 in response to a relative movement between the ring 32 and the seal 31.

Figure 11:
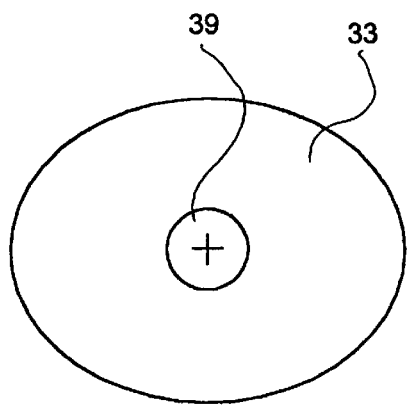
FIG. 11 illustrates a top view of a piercing ring constructed in accordance with the invention.
Figure 12:
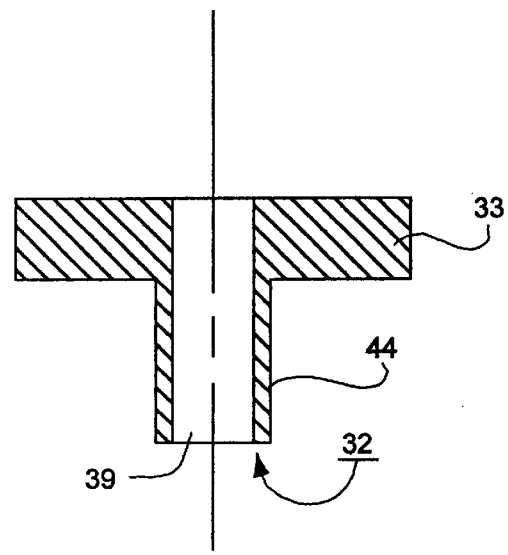
FIG. 12 illustrates a side view of the piercing ring of FIG. 11.

As shown in FIG. 12, the piercing ring 32 has a flange 33 at one end and a tubular portion 44 that defines a central bore 39. As shown in FIG. 11, the flange 33 is of elliptical shape.

As shown in FIG. 8, the tubular portion 44 of the piercing ring 32 is positioned within a recess defined by an annular shoulder 43 on the seal 31 and is frictionally held in place in alignment with the slit 41.

Referring to FIG. 7, the introducer needle assembly includes a hub 13 that is insertable in the catheter hub 11 and an introducer needle 14 that passes through the piercing ring 32 in spaced relation, through the slit 41 in the seal 31 in seal tight manner and through the cannula 12. The slit 41 is opened by the sharpened end of the introducer needle 14 as the needle 14 passes through the seal 31 and into the cannula 12. The bloodless catheter is supplied to a user in this condition prior to use.

After a venipuncture or arterial puncture is made and the introducer needle 14 and cannula 12 placed in a patient, the introducer needle 14 and associated hub 13 are removed. The seal 31, being under a compressive force due to the interference of the wall of the bore 24 with the larger diameter of the seal 31, then seals off the hub 11 in a manner as indicated in FIG. 8 so that blood is prevented from flowing from the patient and the bore 24 out of the hub 11.

Figure 9:
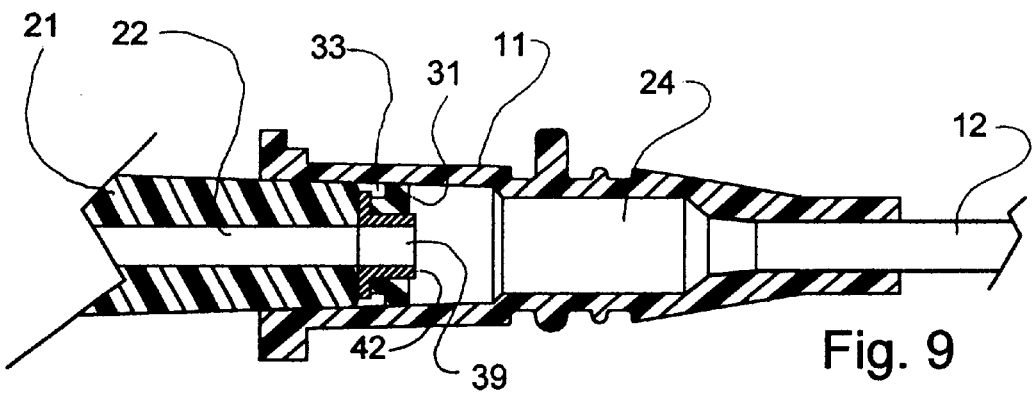
FIG. 9 illustrates a view similar to FIG. 8 with a male luer partially inserted in the hub.

Referring to FIG. 9, a hook-up to an IV bag (not shown) is performed by inserting a means such as a male luer adaptor (connector) 21 into the female luer catheter hub 11. As the male luer adaptor 21 enters the bore 24 of the hub 11, the flange 33 of the piercing ring 32 is encountered. The adaptor 21 then pushes the piercing ring 32 forwardly causing the tubular portion 44 to open the slit 41 in the seal 31 to thereby create a permanent lumen (opening) through the seal 31. The resistance to the piercing ring 32 going through the slit 41 is less than the resistance of the septum seal 31 against the side wall of the bore 24.

Figure 10:
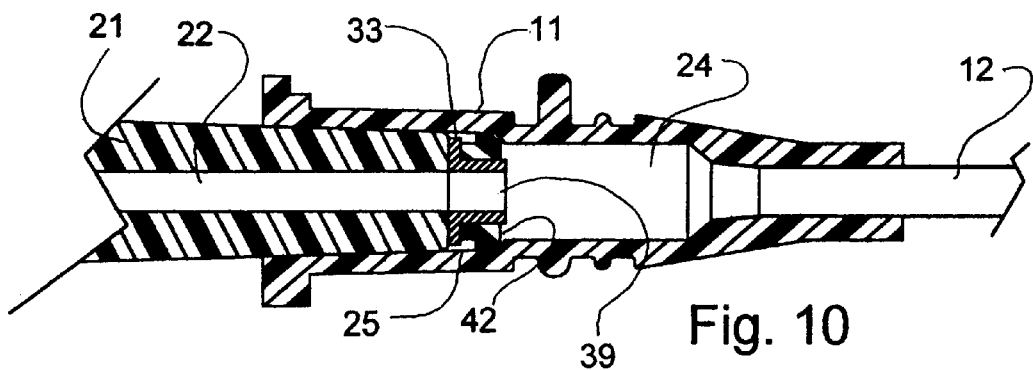
FIG. 10 illustrates a view similar to FIG. 9 with the male luer adaptor secured within the hub.

When the piercing ring 32 has bottomed out within the septum seal 31, the ring 32 and seal 31 composite now move forwardly upon the application of further force by the male adaptor 21 until an interference fit is obtained between the male adaptor 21 and the bore 24 of the hub 11 as indicated in FIG. 10. A connection is now effected and fluids may move from the IV bag through the cannula 12 and into the patient.

It is not necessary that the septum seal 31 be positioned as shown and moved during the connection process. The septum seal 31 and piercing ring 32 may be permanently positioned at a deeper location within the hub 11. In this instance, the tubular portion 44 of the ring 32 would be longer to provide for tolerances encountered as stated in the ANSI/ISO/AMMI specifications for luer connectors.

The piercing ring 32 may be metallic or plastic. The elliptical shape of the flange 33 is to ensure that a portion of the nose 25 of the adaptor 21 is contacted during engagement of the adaptor with the ring 32. Most male luer adaptors have an internal lumen of 0.100 inches or less. However, some have lumens as large as 0.125 inches. To provide for these lumens and the tolerances normally encountered in commercial luer connectors, it has been found that a somewhat elliptical piercing ring flange 33 will meet these requirements. In most cases, a circular piercing ring flange is acceptable. Other configurations, such as a bar laying across the tubular portion are acceptable.

In one embodiment, the septum seal of FIG. 8 was made of silicone having a Durometer of D-50. However, other elastomeric materials and durometers may be used. The seal also had a diameter of 0.175 inches with a thickness at the catheter hub wall of 0.090 inches. The recess defined by the shoulder 43 was 0.040 inches in diameter with a depth of 0.050 inches.

The flange 33 of the piercing ring 32 had a major diameter of 0.145 inches while the tubular portion 44 had a length of 0.100 inches and an outer diameter of 0.045 inches.

The catheter hub bore 24 had a diameter of 0.160 inches at the location where the septum seal 31 was initially positioned.

When positioned within the septum seal 31, the interference fit between the ring 32 and the seal 31 was sufficient to hold the ring 32 in place with no concern that the ring would accidentally be dislodged.

Figure 13:
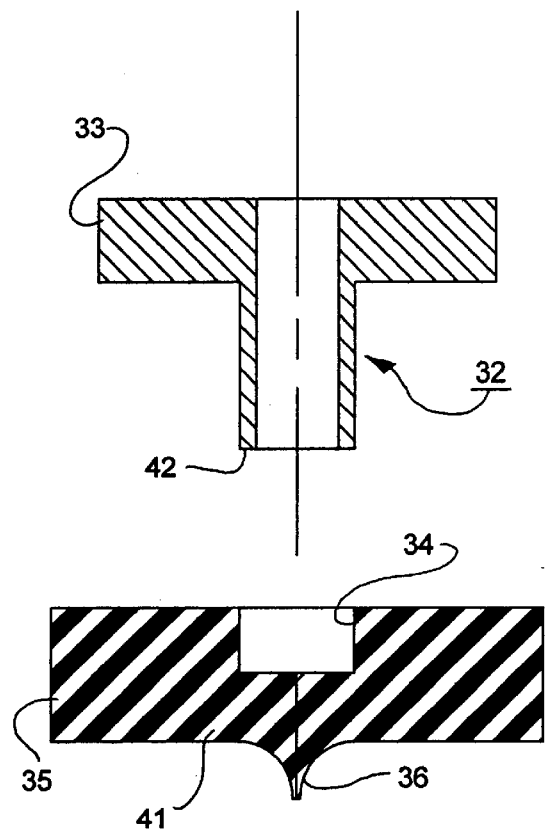
FIG. 13 illustrates an exploded view of the piercing ring of FIG. 12 with a modified seal with a duck bill configuration in accordance with the invention.
Figure 14:
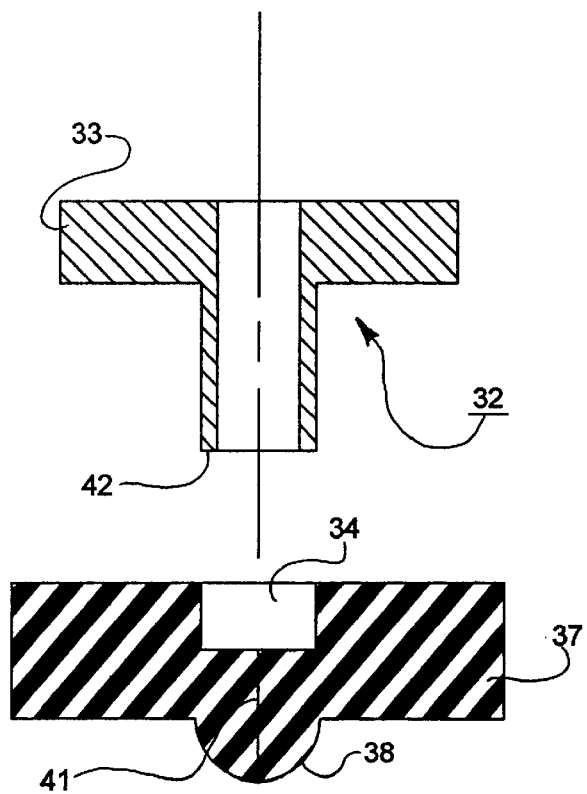
FIG. 14 illustrates an exploded view of the piercing ring of FIG. 12 with another modified seal with a bullet configuration in accordance with the invention.

After removal of the introducer needle 14 and pressure testing, it was found that the leakage pressure of a configuration as shown in FIG. 8 exceeded 20 psi. Under similar conditions but with a septum seal having a duck bill configuration 36 as shown in FIG. 13, the leakage pressure was 50% higher. Also, with a septum seal having a bullet configuration 38 as shown in FIG. 14, the leakage pressure was even higher.

Figure 15:
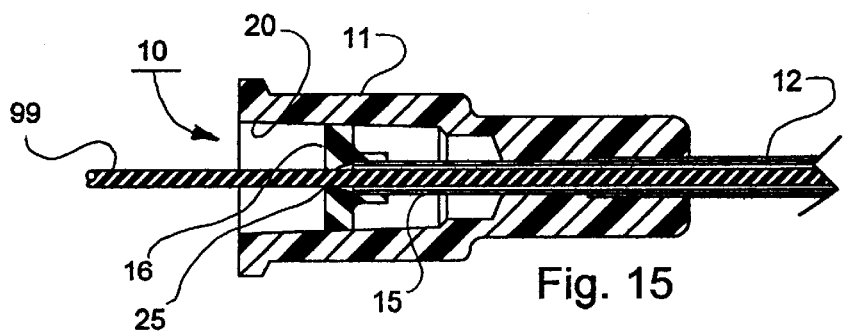
FIG. 15 illustrates a cross-sectional view of the catheter with a guide wire extending through the seal.

Referring to FIG. 15. wherein like reference characters indicate like parts as above, a guide wire 99 or a stylet (not shown) or the like may be passed through the weakened section of the seal 16 and into and through the cannula for insertion into a blood vessel of a patient in a conventional manner. Upon withdrawal of the wire 99, the seal 16 closes to seal off the hub 11.

The invention thus provides an over-the-needle product for making a bloodless venipuncture or arterial puncture while effecting a one time use sterile connection. The product is particularly useful in making a bloodless venipuncture for introducer needles, especially employing the Seldinger Technique. The product effects a fluid retaining puncture and functions as a hook-up product for epidural and other spinal procedures, and other procedures such as angiography and radiology where guide wire placement is required.

The invention further provides a product comprised of a hub, cannula and septum seal within the hub which can be used for other purposes. For example, a guide wire or stylet could be passed through the septum seal and through the cannula. Also, the product may be used with a needle whereby the needle may pierce through the septum need from tie-to-time to infuse fluid into a front vessel of a patient. Upon withdrawal of the needle, the septum seal would again seal off the cannula from an outside environment.

What is claimed is:

1. A bloodless catheter comprising
   a first hub having a bore at a proximal end;
   a cannula fixed in and extending from an opposite distal end of said hub for invasive positioning in a blood vessel; and
   a septum seal mounted in said bore of said hub in circumferentially sealed relation to prevent a flow of fluid from said cannula to said proximal end of said hub, said seal having a weakened central section.

2. A bloodless catheter as set forth in claim 1 wherein said seal is made of elastomeric material.

3. A bloodless catheter as set forth in claim 1 wherein said weakened section of said seal has a slit therein to define a valve.

4. A bloodless catheter as set forth in claim 1 wherein said seal is slidably mounted in said bore.

5. A bloodless catheter as set forth in claim 1 wherein said seal is mounted at one end of said bore with a face thereof exposed for swabbing.

6. A bloodless catheter as set forth in claim 1 further comprising first means in said hub for forming a flow path through said weakened section of said seal in response to a relative movement between said means and said seal.

7. A bloodless catheter as set forth in claim 6 wherein said first means is a tube mounted in said weakened section of said seal and extending into said cannula.

8. A bloodless catheter as set forth in claim 7 wherein said seal has a tubular portion receiving said tube in stretch-fit manner and a centrally disposed slit.

9. A bloodless catheter as set forth in claim 7 which further comprises second means for moving said seal over said tube to cause said tube to pass through said weakened section of said seal.

10. A bloodless catheter as set forth in claim 6 wherein said first means is a piercing ring mounted on said seal for pushing through said weakened section of said seal in a direction towards said cannula to define a flow path through said seal.

11. A bloodless catheter as set forth in claim 10 which further comprises second means for moving said piercing ring through said weakened section of said seal.

12. A bloodless catheter as set forth in claim 11 wherein said second means is a male luer adaptor slidably mounted in said bore of said hub in sealed relation and engaging said ring to push said ring through said weakened section of said seal.

13. A bloodless catheter as set forth in claim 6 which further comprises second means for moving said first means relative to said seal.

14. A bloodless catheter as set forth in claim 13 wherein said second means is a male luer adaptor slidably mounted in said bore of said hub in sealed relation and engaging said septum seal in sealed relation.

15. A bloodless catheter as set forth in claim 1 which further comprises
   a needle hub telescopically mounted in said bore of said first hub; and an introducer needle fixed in said needle hub and extending through said seal in sealed relation and through said cannula.

16. A bloodless catheter as set forth in claim 1 which further comprises a guide wire extending through said weakened section of said seal and said cannula.

17. A bloodless catheter as set forth in claim 1 which further comprises a stylet extending through said weakened section of said seal and said cannula.

18. A bloodless catheter as set forth in claim 1 wherein said cannula is a needle with a sharpened tip.

19. In combination
   first hub having a bore at a proximal end, a cannula fixed in and extending from an opposite distal end of said hub, a septum seal mounted in said bore of said hub in circumferentially sealed relation to prevent a flow of fluid from said cannula to said proximal end of said hub, and a tube mounted in said seal in sealed relation and extending into said cannula;
   a needle hub telescopically mounted in said bore of said first hub and an introducer needle fixed in said needle hub and extending through said seal in sealed relation and through said cannula; and
   a male luer adaptor for slidable mounting in said bore of said first hub after withdrawal of said needle hub therefrom, said adaptor being sized to engage and push said seal over said tube while receiving said tube therein in concentric relation.

20. In combination
   a first hub having a bore at a proximal end, a cannula fixed in and extending from an opposite distal end of said hub, a septum seal mounted in said bore of said hub in circumferentially sealed relation, said seal having a centrally disposed slit to define a valve, and a piercing ring mounted on said seal concentrically of said slit;
   a needle hub telescopically mounted in said bore of said first hub and an introducer needle fixed in said needle hub and extending through said seal in sealed relation and through said cannula; and
   a male luer adaptor for slidable mounting in said bore of said first hub after withdrawal of said needle hub therefrom, said adaptor being sized to engage and push said piercing ring through said slit in said seal to communicate said adaptor with said cannula.

* * * * *

UNITED STATES PATENT AND TRADEMARK OFFICE
CERTIFICATE OF CORRECTION

PATENT NO. : 6,699,221 B2
DATED : March 2, 2004
INVENTOR(S) : Vincent L. Vaillancourt It is certified that error appears in the above-identified patent and that said Letters Patent is hereby corrected as shown below:

<u>Column 3,</u>
Lines 29 to 30, delete "to tube 15 seal (interference fit)".
Line 33, after "positioned" insert -- and --.

<u>Column 7,</u>
Line 28, delete "need".
Line 29, change "front" to -- blood --.

Signed and Sealed this

Fifteenth Day of June, 2004

JON W. DUDAS
*Acting Director of the United States Patent and Trademark Office*

(12) INTER PARTES REEXAMINATION CERTIFICATE (944th)
United States Patent
Vaillancourt

(10) Number: US 6,699,221 C1
(45) Certificate Issued: Aug. 25, 2014

(54) BLOODLESS CATHETER

(75) Inventor: Vincent L. Vaillancourt, Livingston, NJ (US)

(73) Assignee: VLV Associates, Inc., East Hanover, NJ (US)

Reexamination Request:
No. 95/000,565, Aug. 12, 2010

Reexamination Certificate for:
Patent No.: 6,699,221
Issued: Mar. 2, 2004
Appl. No.: 09/879,872
Filed: Jun. 12, 2001

Certificate of Correction issued Jun. 15, 2004

Related U.S. Application Data

(60) Provisional application No. 60/211,733, filed on Jun. 15, 2000.

(51) Int. Cl.
*A61M 5/178* (2006.01)

(52) U.S. Cl.
USPC ............ 604/167.01; 604/164.13; 604/167.03; 604/167.04; 604/167.06

(58) Field of Classification Search
None
See application file for complete search history.

(56) References Cited

To view the complete listing of prior art documents cited during the proceeding for Reexamination Control Number 95/000,565, please refer to the USPTO's public Patent Application Information Retrieval (PAIR) system under the Display References tab.

*Primary Examiner* — Andres Kashnikow

(57) ABSTRACT

The over-the-needle catheter is provided with a septum seal within the hub of the catheter. The introducer needle passes through the septum seal and into the catheter. Upon removal of the introducer needle, the septum seal reseals so that blood is prevented from flowing from the patient out of the hub. A male luer adaptor is used to form a connection, for example, to an IV bag by pushing the seal onto a tube secured within the hub and communicating with the catheter or, in another embodiment, by pushing a piercing ring through a slit in the septum seal to form a permanent lumen.

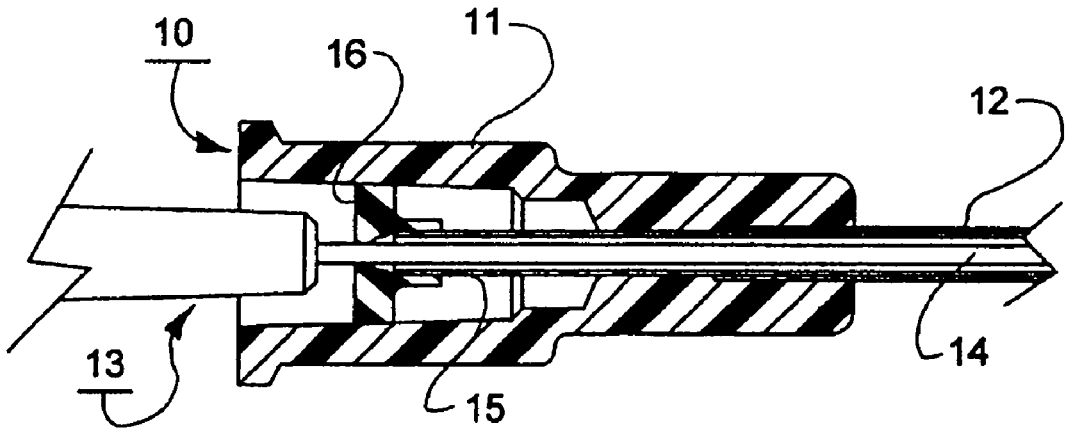

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1-20 are cancelled.

\* \* \* \* \*